United States Patent [19]
Sprecker et al.
[11] 4,235,729
[45] Nov. 25, 1980

[54] 2-OXABICYCLOOCTANE DERIVATIVES, PROCESSES FOR PREPARING SAME AND ORGANOLEPTIC USES THEREOF

[75] Inventors: Mark A. Sprecker, Sea Bright; Frederick L. Schmitt, Holmdel; Manfred H. Vock, Locust; Joaquin F. Vinals, Red Bank, all of N.J.; Jacob Kiwala, Brooklyn, N.Y.

[73] Assignee: International Flavors & Fragrances, Inc., New York, N.Y.

[21] Appl. No.: 52,335

[22] Filed: Jun. 27, 1979

Related U.S. Application Data

[60] Division of Ser. No. 8,924, Feb. 2, 1979, Pat. No. 4,197,328, which is a continuation-in-part of Ser. No. 953,128, Oct. 20, 1978, Pat. No. 4,195,099.

[51] Int. Cl.[3] .......................... A61K 7/46; C11D 3/20
[52] U.S. Cl. ...................................... 252/8.9; 252/8.6; 252/522 R
[58] Field of Search ..................... 426/536; 260/345.1; 252/8.9, 522

[56] References Cited

U.S. PATENT DOCUMENTS

| | | | |
|---|---|---|---|
| 4,128,729 | 12/1978 | Sanders et al. | 252/522 |
| 4,170,599 | 10/1979 | Bennett | 260/345.2 |

OTHER PUBLICATIONS

Chem. Abs. 88:177030C "Use of a Bicyclic Oxygen-Cont. Compt. as Perfume and/or Aroma Ingredient," Schulte-Elte, K. H. Feb. 28, 1978.
J. Org. Chem., vol. 35(7), pp. 2386-2390 (1970), Givdici et al. (QD241-J6), "Synthesis of 2-Oxabicyclo[222]octane Reg. No. 280-39-7.
Tetrahedron Lett. (49), 4281-4284 (1970), Scheider et al., "Synthesis of 2-Oxabicyclo[222]Octane," Reg. No. 280-39-7.

*Primary Examiner*—Joseph L. Schofer
*Assistant Examiner*—Herbert J. Lilling
*Attorney, Agent, or Firm*—Arthur L. Liberman

[57] ABSTRACT

Described are derivatives of 2-oxabicyclo[2.2.2]octanes and precursors therefor, cyclohexenemethanols as well as lower alkyl esters of said cyclohexenemethanols. The oxabicyclooctanes are useful in perfumery and foodstuff and medicinal product flavors. The cyclohexenemethanols are useful as precursors for the oxabicyclooctanes.

5 Claims, 9 Drawing Figures

GLC PROFILE FOR EXAMPLE I

NMR SPECTRUM FOR EXAMPLE I

IR SPECTRUM FOR EXAMPLE I.

GLC PROFILE FOR EXAMPLE II.

NMR SPECTRUM FOR EXAMPLE II.

IR SPECTRUM FOR EXAMPLE II

GLC PROFILE FOR EXAMPLE III.

NMR SPECTRUM FOR EXAMPLE III, FRACTION 17.

I R SPECTRUM FOR EXAMPLE III, FRACTION 17

2-OXABICYCLOOCTANE DERIVATIVES, PROCESSES FOR PREPARING SAME AND ORGANOLEPTIC USES THEREOF

This application is a divisional of application Ser. No. 008,924, filed Feb. 2, 1979, now U.S. Pat. No. 4,197,328 which is a continuation-in-part of Application for United States Letters Patent, Ser. No. 953,128 filed Oct. 20, 1978 now Patent No. 4,195,099.

BACKGROUND OF THE INVENTION

The instant invention provides novel oxabicyclooctanes having the structure:

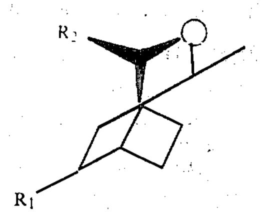

wherein $R_1$ is hydrogen or methyl and $R_2$ is $C_4$ or $C_5$ alkyl or $C_3$ alkenyl as well as intermediates for producing same having the generic structure:

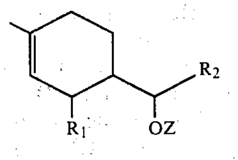

wherein $R_1$ is hydrogen or methyl; $R_2$ is $C_4$ or $C_5$ alkyl or $C_3$ alkenyl; and wherein Z is hydrogen or MgX and wherein X is chloro, bromo or iodo. The said oxabicyclooctanes are useful for their organoleptic properties in consumable materials.

Chemical compounds which can provide sweet, green, anisic, natural, sweet warm herbaceous, clean herbaceous, minty camphoraceous, black pepper-like aromas with carvone (caraway), tagette nuances and basil topnotes are desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

By the same token, materials which can provide eucalyptus, herbaceous, citrus, woody, lime, blueberry, mushroom-like, fennel, spicey and black pepper-like aromas and eucalyptus, herbaceous, citrus, bergamot-like sweet, blueberry, fruity, mushroom-like, fennel, creamy, chocolate-like, spicey and black pepper-like flavor characteristics with cooling nuances are desirable in applying the art of flavoring to foodstufffs, toothpastes, chewing gums and medicinal products. Many of the natural materials which provide such flavor notes and contribute desired nuances to flavoring compositions are high in cost, vary in quality from one batch to another and/or are generally subject to the usual variations in natural products.

There is, accordingly, a continuing effort to find synthetic materials which will replace, enhance or augment the essential flavor and fragrance notes provided by natural essential oils or compositions thereof. Unfortunately, many of these synthetic materials either have the desired nuances only to a relatively small degree or else contribute undesirable or unwanted odor to the compositions. The search for materials which can provide a more refined citrus, blueberry or mushroom or chocolate or black pepper flavor, for example, has been difficult and relatively costly in the areas of both natural products and synthetic products.

Artificial flavoring agents for foodstuffs have received increasing attention in recent years. For many years, such food flavoring agents have been preferred over natural flaovring agents at least in part due to their diminished cost and their reproducible flavor qualities. For example, natural food flavoring agents such as extracts, concentrates and the like are often subject to wide variations due to changes in quality, type and treatment of the raw materials. Such variations can be reflected in the end products and result in unfavorable flavor characteristics in said end product. Additionally, the presence of the natural product in the ultimate food may be undesirable because of increased tendency to spoil. This is particularly troublesome in food and food uses where such products as dips, soups, chips, sausages, gravies and the like are apt to be stored prior to use.

The fundamental problem in creating artificial flavor agents is that the artificial flavor to be achieved be as natural as possible. This generally proves to be a difficult task since the mechanism for flavor development in many foods, medicinal products, chewing gums and toothpastes is not completely known. This is noticeable in products having citrus, blueberry, mushroom, chocolate and black pepper flavor characteristics, particularly.

Even more desirable are products that can serve to substitute for difficult-to-obtain natural perfumery oils and at the same time substitute for natural flavoring ingredients in foodstuffs, chewing gums, medicinal products and toothpastes and in addition, at the same time, substitute for natural flavoring ingredients in tobaccos.

Arctander in "Perfume and Flavor Chemicals (Aroma Chemicals)", Vol. I, 1969 at monograph No. 616 describes 1,8-cineole having the structure:

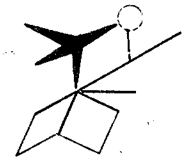

as being useful in perfumery and in flavor compositions. Thus, Arctander states, regarding 1,8-cineole:

"Fresh, diffusive, camphoraceous-cool odor of poor tenacity. Sweet and fresh, cool-camphoraceous taste and cool mouthfeel unless very highly concentrated.

Widely used in perfume compositions for its refreshing effect in herbaceous type fragrances, Lavender, New Mown Hay, Fougere, etc. and in medicinal type odors for soap and household products. Also, in masking odors for industrial purposes, unless Eucalyptus oil must be used for its lower cost.

This oxide has found increased usage during the 1965/66 period of abnormally high prices for Lavandin and Spike Lavender oils.

The odor of Eucalyptus is, in some countries, rated synonomous with masking odors for lavatories, etc., a fact which has an unquestionable psychological effect, causing people to reject the odor of Eucalyptus for oral-hygienic purposes, etc. Similar viewpoints has been observed about the use of Methylsalicylate in dentifrice in many European countries. Peculiarly enough, Methylsalicylate is still a popular candy-, soft-drink-and toothpaste flavor in the U.S.A., where the ester at the same time is used as a masking agent in toilet-bowl cleaners!

The 'olfactory association' is quite human and common, but it may at times completely destroy the chances of a chemical from its use in flavors or other field.

Eucalyptol is extensively used in flavor compositions, particularly in all types of preparations for oral hygiene, dentifrice, breath-sprays, mouthwashes, cough lozenges, pastilles, skin rubbing lotions, inhalator fluids, etc. It seems, however, that its use in skin rubbing lotions has hampered its popularity as a candy flavor in the U.S.A.

Normal use concentrations are about 1 to 15 ppm in the finished (flavored) product, but concentrations as high as 200 ppm are found in chewing gum."

Furthermore, the compound having the structure:

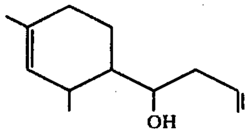

and the compound having the structure:

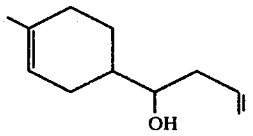

are reported by Sopov and Kovner at Zh. Obsch. Khim. 34, 1492-6 (1964) as abstracted in Chem. Abstracts, Vol. 61, 5529b.

The Sopov and Kovner reference does not, however, disclose organoleptic uses of the compounds having the structures:

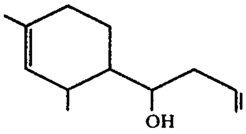
and
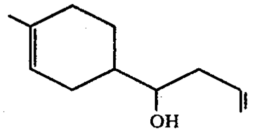

Furthermore, nothing in the prior art discloses any of the compounds having the generic structure:

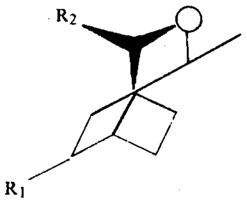

wherein $R_1$ is hydrogen or methyl and $R_2$ is $C_4$ or $C_5$ alkyl or $C_3$ alkenyl and nothing in the prior art discloses the use as an intermediate of the genus having the structure:

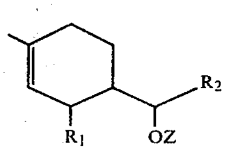

wherein $R_1$ is hydrogen or methyl; $R_2$ is $C_4$ or $C_5$ alkyl or $C_3$ alkenyl; and Z is hydrogen of MgX wherein X is chloror, bromo or iodo.

Insofar as their organoleptic uses are concerned, the compound of the instant invnention have unexpected, unobvious and advantageous properties over such compounds of the prior art as 1,8-cineole.

THE INVENTION

Figure 1:
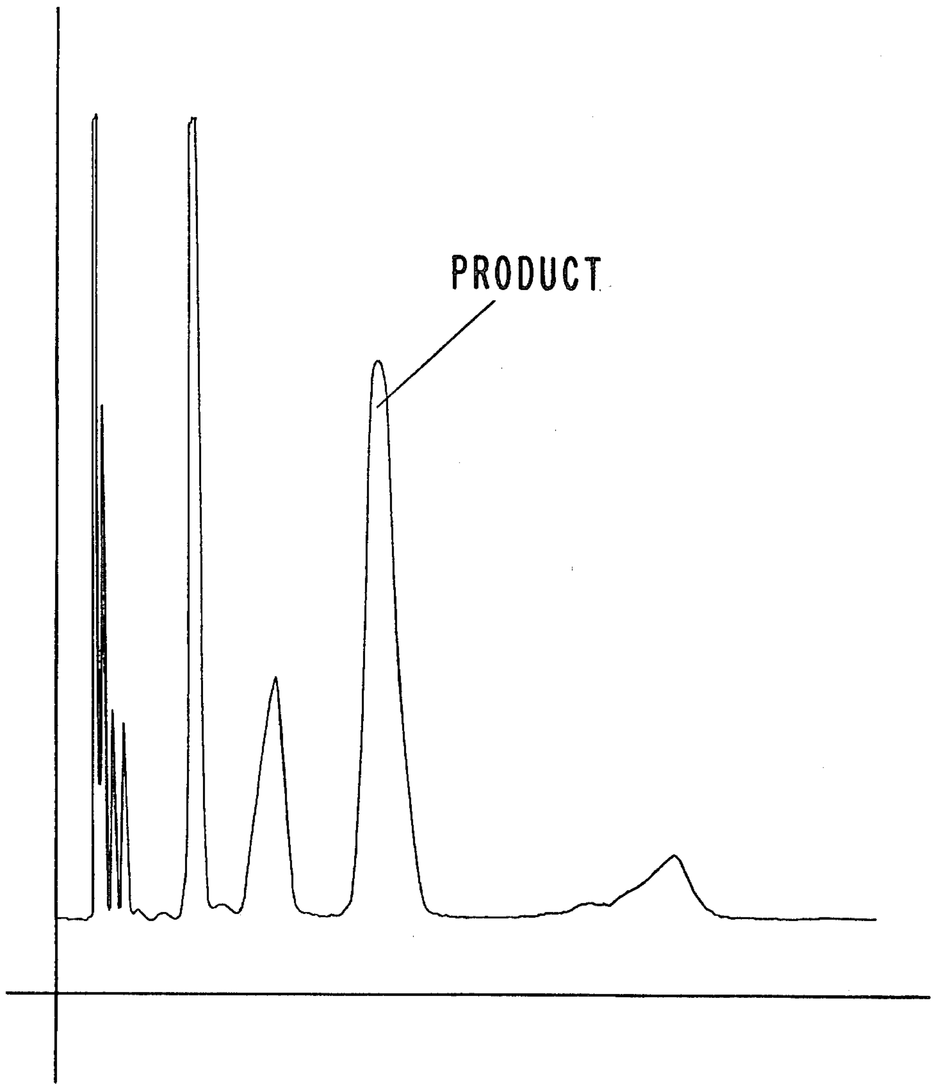
FIG. 1 is the GLC profile for the product produced according to Example I, 3(2'-butyl)-1,5-dimethyl-2-oxabicyclo [2.2.2]octane.

It has now been determined that certain oxabicyclooctanes are capable of imparting a variety of flavors and fragrances to various consumable materials and are also capable of augmenting or enhancing a variety of flavors and fragrances of various consumable materials.

Briefly, our invention contemplates augmenting or enhancing the flavors and/or fragrances of such consumable materials as perfumes, perfumed articles, colognes, foodstuffs, chewing gums, toothpastes and medicinal products by adding thereto a small but effective amount of at least one of the compounds having the generic structure:

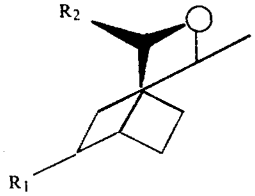

wherein $R_1$ is hydrogen or methyl; $R_2$ is $C_4$ or $C_5$ alkyl or $C_3$ alkenyl.

The oxabicyclooctane derivatives of our invention augment or enhance eucalyptus, herbaceous, citrus, woody, lime, blueberry, mushroom-like, fennel, spicey and black pepper-like aroma characteristics and eucalyptus, herbaceous, citrus, bergamot-like, sweet, blueberry, fruity, mushroom-like, fennel, creamy, chocolate-like, spicey and black pepper-like flavor characteristics and cooling nuances insofar as augmenting or enhancing the aroma or taste of foodstuffs, toothpastes, medicinal products, and chewing gums.

The oxabicyclooctane derivatives of our invention also augment or enhance the sweet, green, anisic, natural sweet warm herbaceous, clean herbaceous, minty camphoraceous, black pepper, carvone (caraway-like), tagette and basil aroma characteristics of perfumes, perfumed articles and colognes of our invention.

Examples of the oxabicyclooctane derivatives of our invention and their organoleptic characteristics are as follows:

nol. The organometallic salt of the cyclohexene carbinol is then hydrolyzed (in the presence of acid) to form a cyclohexene carbinol of our invention. This reaction product is further reacted by cyclizing the compound to form the desired 2-oxabicyclo[2.2.2]octane. The overall reaction sequence described above is as follows:

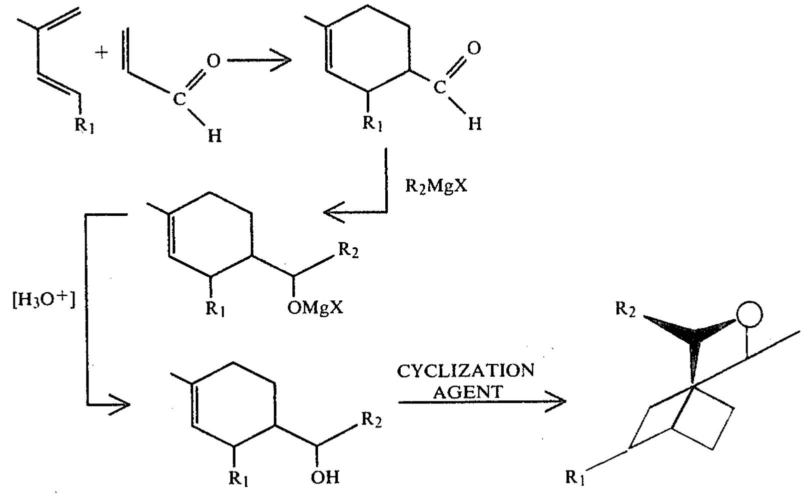

The Diels-Alder reaction of the α,β-unsaturated aldehyde with the conjugated diene is a procedure well known in the prior art. The reaction may be carried out in the presence of a Lewis acid catalysts such as zinc chloride, aluminum chloride or aluminum bromide; or it may be carried out in the absence of catalysts at higher temperatures, e.g., 50° C. up to 150° C. When carrying out the Diels-Alder reaction in the presence of catalysts, lower temperatures, e.g., −10° C. up to 30° C. may be utilized.

| STRUCTURE OF COMPOUND | NAME OF COMPOUND | FLAVOR CHARACTERISTICS | FRAGRANCE CHARACTERISTICS |
|---|---|---|---|
| 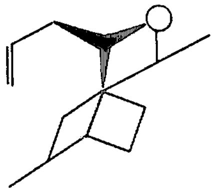 | 3-allyl-1,5-dimethyl-2-oxabicyclo[2.2.2] octane | A eucalyptus, herbaceous, citrus, woody, lime and blueberry aroma profile with a eucalyptus, herbaceous, citrus, woody, lime, blueberry, bergamot-like, sweet, fruity flavor characteristic with cooling nuances. | A clean herbaceous, minty camphoraceous aroma with carvone (caraway) tagette nuances and good basil topnotes. |
| 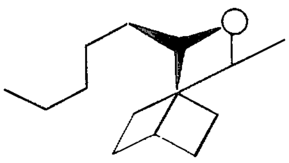 | 1-methyl-3-n-pentyl-2-oxabicyclo[2.2.2] octane | A mushroom, herbaceous and fennel aroma character with a mushroom, herbaceous, fennel, creamy and chocolate-like flavor character. | A sweet green anisic aroma. |
| 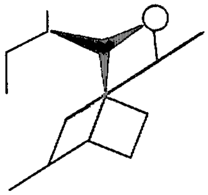 | 3-n-butyl-1,5-dimethyl-2-oxabicyclo [2.2.2]octane | A herbaceous, spicey and black pepper aroma with a herbaceous, spicey, black pepper and bitter flavor characteristic at 10 ppm. | A sweet warm herbaceous black pepper aroma. |

The oxabicyclooctane derivatives of our invention can be produced by first forming a cyclohexene carboxaldehyde by reaction of an α,β-unsaturated aldehyde with a conjugated diene. The resulting cyclohexene carboxaldehyde is then reacted with a Grignard reagent to form an organometallic salt of the cyclohexene carbi- That part of the reaction sequence whereby the cyclohexene carboxaldehyde is reacted with the Grignard reagent to form the cyclohexene carbinol organometallic salt followed by hydrolysis of the cyclohexene carbinol organometallic salt to form the cyclohexene carbinol followed by cyclization of the resulting cyclohexene carbinol to form the 2-oxabicyclo[2.2.2]octane may be carried out either in one step or in two steps.

In carrying out the "two-step reaction" whereby the cyclohexene carbinol is first isolated and then cyclized in the first step, that is, in the reaction of the Grignard reagent with the cyclohexene carboxaldehyde, the mole ratio of alkyl halide or alkenyl halide to magnesium in order to form the Grignard reagent is from 0.9:1 up to 1.5:1. The mole ratio of alkyl halide or alkenyl halide to cyclohexene carboxaldehyde is from 0.8:1 up to 1.5:1 This reaction of the Grignard reagent with the cyclohexene carboxaldehyde takes place in an ether solvent such as diethyl ether, tetrahydrofuran or di-n-butyl ether or another inert solvent such as toluene, chloroform or benzene to which two equivalents of ether has been added. The temperature of reaction preferably is between 0° and 100° C. with the most preferred temperature range for this reaction being from 35° C. up to 45° C.

In the two-step reaction, the resulting cyclohexene carbinol is then isolated as by distillation. The resulting cyclohexene carbinol is then cyclized at a temperature in the range of from 25° C. up to 150° C. in the presence of an acid such as aqueous hydrochloric acid or sulfuric acid or phosphoric acid. This acid may be used in combination with an alcohol such as isopropyl alcohol or with some other solvents such as tetrahydrofuran or acrylonitrile or the acid may be used by itself to effect the cyclization. The cyclization in the alternative may be carried out using a Lewis Acid such as borontrifluoride, aluminum trichloride, zinc chloride, stannic chloride or zinc bromide in the presence of a solvent such as toluene, chloroform or xylene.

As stated above, the reaction of the cyclohexene carboxaldehyde to form the cyclohexene carbinol followed by cyclization may take place in a single reactor without separation of the cyclohexene carbinol. The conditions are the same as stated above for the two-step reaction.

The individual oxabicyclooctane derivatives of our invention can be obtained in pure form or in substantially pure form by conventional purification techniques. Thus, the products can be purified and/or isolated by distillation, extraction, crystallization, preparative chromatographic techniques (column chromatography and vapor phase chromatography) and the like. It has been found desirable to purify the oxabicyclooctane derivatives of our invention by fractional distillation in vacuo.

When the oxabicyclooctane derivatives of our invention are used as food flavor adjuvants, the nature of the co-ingredients included with said oxabicyclooctane derivatives in formulating the product composition will also serve to alter, modify, augment or enhance the organoleptic characteristics of the ultimate foodstuff treated therewith.

As used herein in regard to flavors, the terms "alter", "modify" and "augment" in their various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible, non-toxic materials which have medicinal value such as cough syrups, cough drops, aspirin and chewable medicinal tablets.

The term "chewing gum" is intended to mean a composition which comprises a substantially water insoluble, chewable plastic gum base such as chicle, or substitutes therefor, including jelutong, guttakay rubber or certain comestible natural or synthetic resins or waxes. Incorporated with the gum base in admixture therewith may be plasticizers or softening agents, e.g., glycerine, and a flavoring composition which incorporates one or more of the oxabicyclooctane derivatives of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterised as flavoring adjuvants or vehicles comprising, broadly, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxy anisole), butylated hydroxytoluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates; starches, pectins, and emulsifiers, e.g., mono- and diglycerides of fatty acids, skim milk powder, hexoses, pentoses, disaccharides, e.g., sucrose, corn syrup and the like.

Surface acive agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditions include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like, firming agents such as aluminum sodium sulfate, calcium chloride and calcium gluconate; texturizers, anticaking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alphamethylbutyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methylbutanal, beta, beta-dimethyl acrolein, methyl n-amyl ketone, n-hexanal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, beta-damascone, alpha-damascone, beta-damascenone, acetophenone, 2-heptanone, o-hydroxy-acetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxy-phenyl-2-ethanol, isoamyl alcohol, isofenchyl alcohol, phenyl-2-ethanol, alpha-terpineol, cis-terpinhydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl carpylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexentyl butyrate, hexyl butyrate, isoamyl acetate, isopropyl butyrate, methyl acetate, methyl butyrate, methyl caproate, methyl isobutyrate, alpha-methyl-phenylglycidate, ethyl succinate, isobutyl cinnamate, cinnamyl formate, methyl cinnamate, and terpenyl acetate; hydrocarbons such as dimethyl naphthalene, dodecane, methyldiphenyl, methyl naphthalene, myrcene, naphthalene, octadecane, tetradecane, tetramethylnaphthalene, tridecane, trimethylnaphthalene, undecane, caryophyllene, alpha-phellandrene, beta-phellandrene, p-cymene 1-alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose, capsicum, yara yara and vanilla; lactones such as γ-nonalactone; sulfides, e.g., methyl sulfide and other materials such as maltol, and acetals (e.g., 1,1-diethoxyethane, 1,1-dimethyloxyethane and dimethoxymethane), piperine, chavicine, and piperidine.

The specific flavoring adjuvant selected for use may be either solid or liquid depending upon the desired physical form of the ultimate product, i.e., foodstuff, whether simulated or natural, and should, in any event, (i) be organoleptically compatable with the oxabicyclooctane derivatives of our invention by not covering or spoiling the organoleptic properties (aroma and/or taste) thereof; (ii) be non-reactive with the oxabicyclooctane derivatives of our invention and (iii) be capable of providing an environment in which the oxabicyclooctane derivatives can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of oxabicyclooocatane derivatives employed in a particular instance can vary over a relatively wide range, depending upon the desired organoleptic effects to be achieved. Thus, correspondingly, greater amounts would be necessry in those instances wherein the ultimate food composition to be flavored, e.g., with a mushroom flavor or a specific black pepper-like flavor) is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of oxabicyclooctane derivatives will, of course, substantially vitiate any possibility of obtaining the desired results while excess quantities prove needlessly costly and in extreme cases may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of bicyclooctane derivatives ranging from a small but effective amount, e.g., 0.05 parts per million up to about 500 parts per million based on total composition, are suitable. Concentrations in excess of the maximum quantity stated are not normally recommended since they fail to provide commensurate enhancement of organoleptic properties. In those instances wherein the bicyclooctane derivatives are added to the foodstuff as an integral component of a flavoring composition, it is, of course, essential that the total quantity of flavoring composition employed be sufficient to yield an effective bicyclooctane derivative concentration in the foodstuff product.

Food flavoring compositions prepared in accordance with the present invention preferably contain the bicyclooctane derivatives in concentrations ranging from about 0.025% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the bicyclooctane derivatives with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix, are obtained by mixing the dried solid components, e.g., starch, sugar and the like, and bicyclooctane derivatives in a dry blender until the requisite degree of uniformity is achieved.

It is presently preferred to combine with the bicyclooctane derivatives of our invention, the following adjuvants: Oil of Cubeb, Phellandrene; β-Phellandrene; Oil of Coriander, Oil of Pimento Leaf, Oil of Patchouli; Natural Lemon Oil; Acetaldehyde; α-Terpineol, Citral; Carvone; Terpinolene; α-Terpinene; Diphenyl; α-Fenchyl Alcohol; Cineole; Limonene; Linalool; Geranyl Acetate; Nootkatone; Neryl Acetate; Heliotropin; Maltol; Vanillin; Ethyl Maltol; Ethyl Vanillin; Anisaldehyde; Alpha Pinene; Beta-Pinene; Beta-Caryophyllene; Dihydrocarveol; Piperonal; Piperine; Chavicine; Piperidine; Oil of Black Pepper; Black Pepper Oleoresin; Capsicum; Oil of Nutmeg; Cardamon Oil; Clove Oil; Spearmint Oil; Oil of Peppermint; and $C_{10}$-Terpinyl Ethers as described in Application for United States Letters Patent, Ser. No. 872,937 filed on January 27, 1978, now U.S. Pat. No. 4,131,687 issued on December 26, 1978 (such as fenchyl ethyl ethers).

The oxabicyclooctane derivatives and the cyclohexene alkyl and alkenyl carbinols and esters of our invention can be used to contribute sweet, green, anisic, natural sweet warm herbaceous, clean herbaceous, minty camphoraceous, black pepper, carvone (caraway), and tagette aromas with basil topnotes to perfumes, perfumed articles and colognes. As olfactory agents, the oxabicyclooctane derivatives and the cyclohexene alkyl and alkenyl carbinols and esters of our invention can be formulated into or used as components of a "perfume composition" or can be used as components of a "perumed article" or the perfume composition may be added to perfumed articles.

The term "perfume composition" is used herein to mean a mixture of organic compounds including, for example, alcohols, aldehydes, ketones, nitriles, ethers other than the oxabicyclooctane derivatives of our invention, lactones, natural essential oils, synthetic essential oils and frequently hydrocarbons which are admixed so that the combined odors of the individual components produce a pleasant or desired fragrance. Such perfume compositions usually contain: (a) the main note or the "bouquet" or foundation stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling, fresh-smelling materials.

In perfume compositions, the individual component will contribute its particular olfactory characteristics, but the overall effect of the perfume composition will be the sum of the effects of each of the ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the oxabicyclooctane derivatives of this invention which will be effective in perfume compositions depends on many factors, including the other ingredients, their amounts and the effects which are desired. It has been found that perfume compositions containing as little as 0.5% of the oxabicyclooctane derivatives of this invention, or even less, can be used to impart an interesting sweet, green, anisic, natural sweet warm herbaceous, clean herbaceous, minty camphoraceous, black pepper, carvone and/or tagette-like aroma with basil topnotes to soaps, liquid and solid cationic, anionic, and nonionic detergents, cosmetics, powders, liquid and solid fabric softeners, optical brightener compositions, and other products. The amount employed can range up to 50% or higher and will depend on considerations of cost, nature of the end product, and the effect desired on the finished product and particular fragrance sought.

The oxabicyclooctane derivatives of this invention can be used alone or in a perfume composition as an olfactory component in detergents and soaps, space odorants and deodorants; perfumes; colognes, toilet waters; bath salts; hair preparations, such as lacquers, brilliantines, pomades, and shampoos; cosmetic preparations, such as creams, deodorants, hand lotions, and sun screens; powders, such as talcs, dusting powders, face powders and the like. When used as an olfactory component of a perfumed article, as little as 0.01% of one or more of the oxabicyclooctane derivatives will suffice to impart an interesting sweet green anisic, natural sweet warm herbaceous, clean herbaceous, minty camphoraceous, black pepper, carvone, tagette-like and/or basil-like aroma. Generally, no more than 0.5% is required.

In addition, the perfume composition can contain a vehicle or carrier for the oxabicyclooctane derivatives alone or with other ingredients. The vehicle can be a liquid such as a non-toxic alcohol such as ethanol, a glycol such as propylene glycol, or the like. The carrier can be an absorbent solid such as a gum or components for encapsulating the composition such as gelatin which can be used to form a capsule wall surrounding the perfume oil, as by means of coacervation.

It will thus be apparent that the oxabicyclooctane derivatives of our invention can be utilized to alter, modify, augment or enhance sensory properties, particularly organoleptic properties, such as flavor(s) and/or fragrance(s) of a wide variety of consumable materials.

The following examples serve to illustrate our invention, and this invention is to be considered restricted thereto only as indicated in the appended claims.

All parts and percentages given herein are by weight unless otherwise specified.

EXAMPLE I

PREPARATION OF 3-(2'-BUTYL)-1,5-DIMETHYL-2-OXABICYCLO [2.2.2]OCTANE

Reaction:

-continued

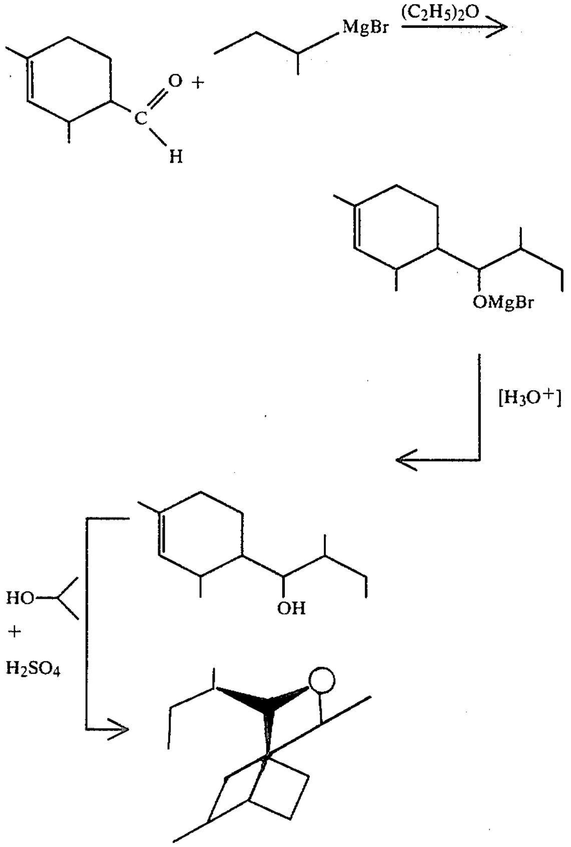

A solution of s-butyl magnesium bromide in ether is prepared by dropwise adding a solution of 473 grams (3.45 moles) of 2-bromobutane in 700 mls of dry ether to a stirred slurry of 76.5 grams of magnesium (3.15 moles) in 600 mls of dry ether under nitrogen at reflux. The resulting solution is stirred at reflux for 30 minutes. A solution of 414 grams of 2,4-dimethyl-3-cyclohexenyl-carboxaldehyde (3 moles) in 200 mls of ether is then added to the reaction mixture over a period of one hour at reflux under nitrogen. The resulting slurry is heated at reflux for 30 minutes and then cooled to 0° C. 1200 grams of 20% (wt/wt) sulfuric acid is slowly added with external cooling over a 30-minute period. After the addition is complete, two clear layers appear. A distillation head is placed on the flask and ether is distilled from the reaction mixture at atmospheric pressure to a pot temperature of 90° C. 300 Grams of isopropyl alcohol is added to the reaction mixture. Sulfuric acid (100 grams) is added slowly and the resulting solution is heated to reflux for ten hours. At the end of this period, the reaction mass is cooled. 500 Ml of water and 100 ml of toluence is added thereto with stirring. The phases are allowed to separate and the aqueous phase is discarded. The organic phase is washed twice with $H_2O$, with sufficient sodium carbonate added to the second wash to adjust the pH to 7–8. Distillation of the organic layer affords 227 grams of 3-(s-butyl-1,5-dimethyl-2-oxabicycol[2.2.2]octane (b.p. 68° C., 1.4 mm).

The NMR and IR spectra show fraction 8 of the distillation.

Figure 2:
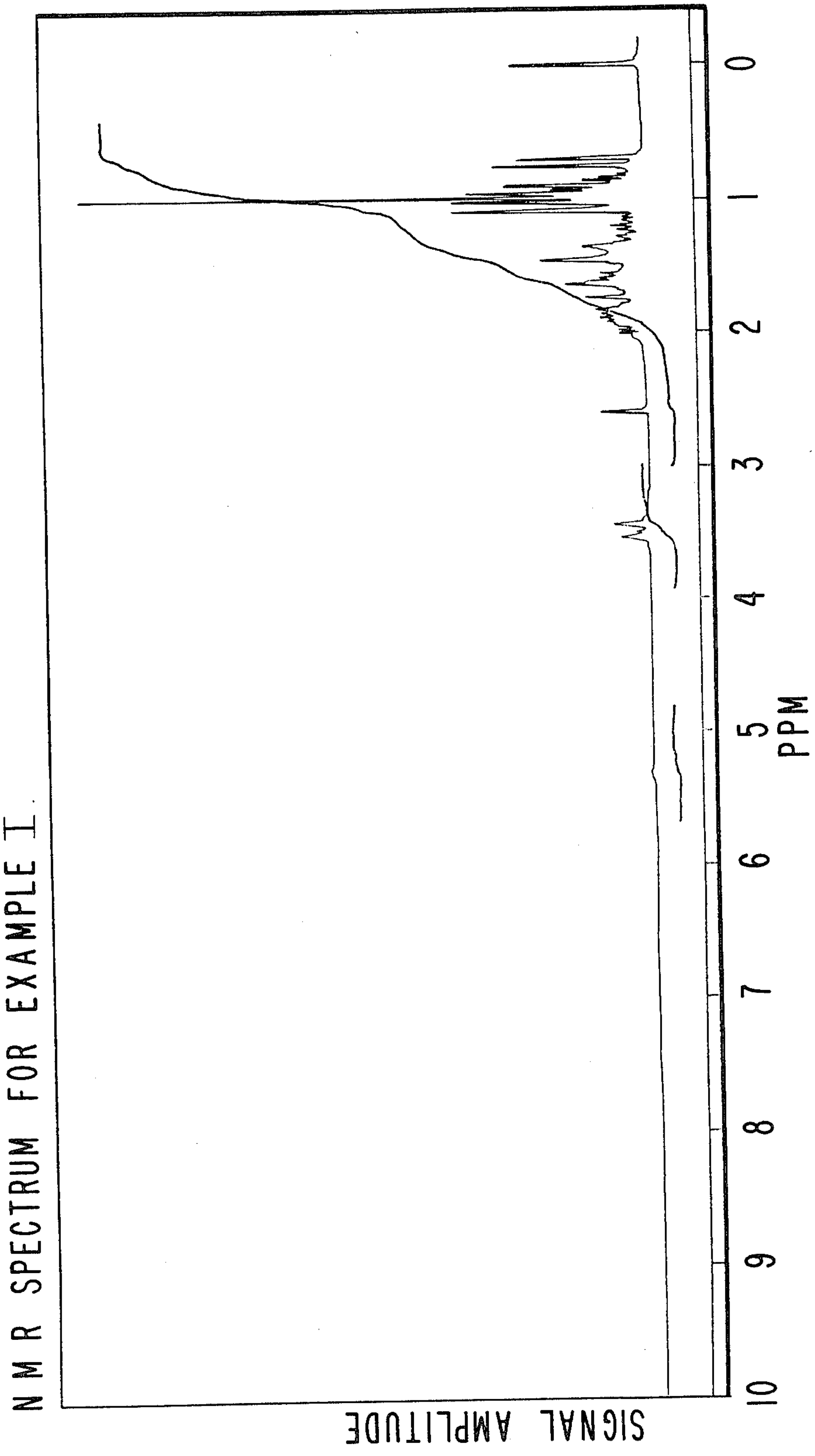
FIG. 2 is the NMR spectrum for the compound produced according to Example I.
Figure 3:
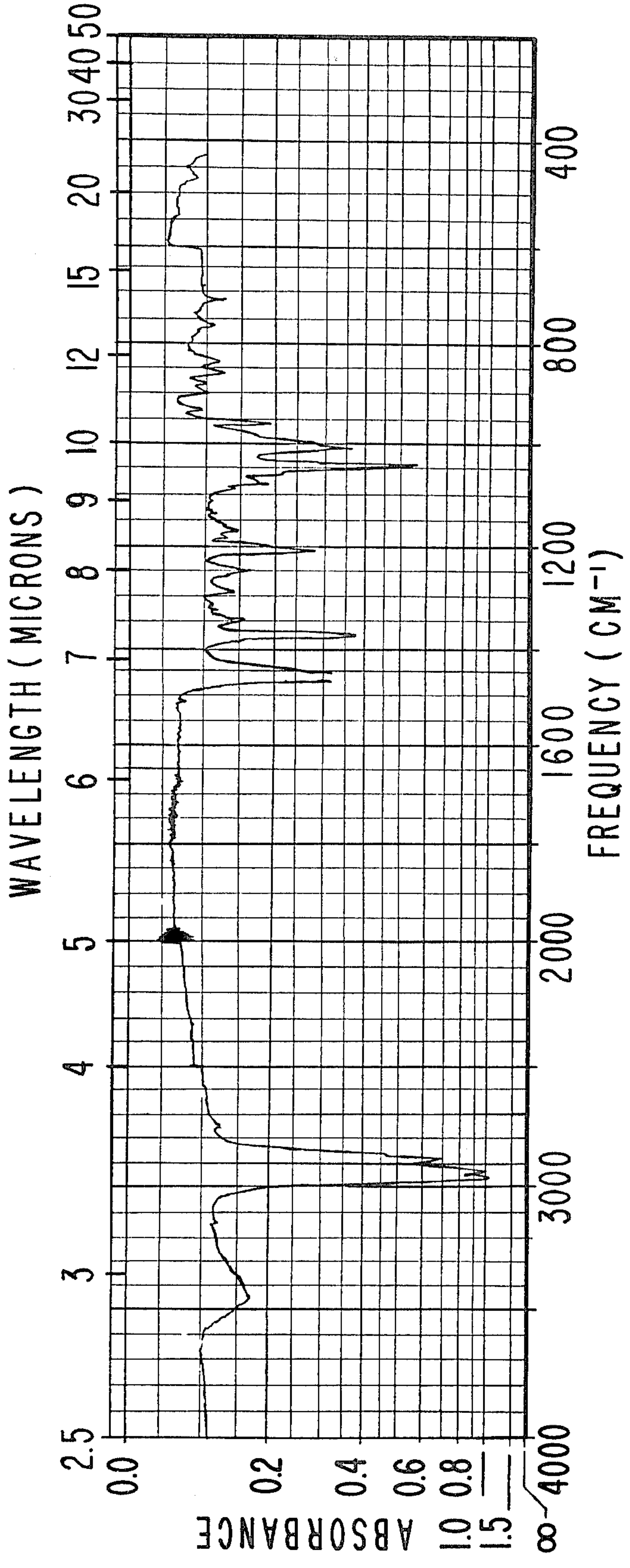
FIG. 3 is the infrared spectrum for the compound produced according to Example I.

FIG. 1 is the GLC profile for the reaction product (Conditions: 180° isothermal; SE-30 column). The NMR spectrum for the resulting reaction product is set forth in FIG. 2. The infrared spectrum for the resulting reaction product is set forth in FIG. 3.

EXAMPLE II

PREPARATION OF 3-ALLYL-1,5-DIMETHYL-2-OXABICYCLO[2.2.2]OCTANE

Reaction:

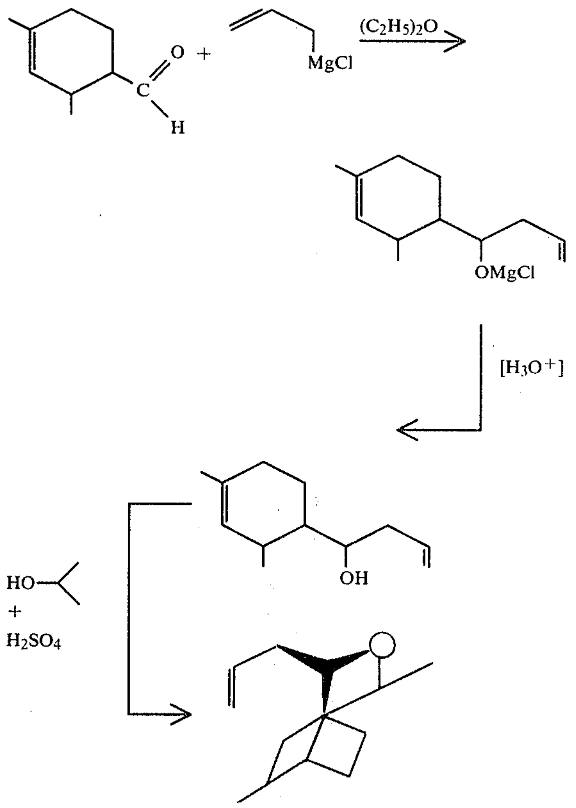

A solution of 264 grams (3.45 moles) of allyl chloride and 414 grams (3 moles) of 2,4-dimethyl-3-cyclohexenyl carboxaldehyde in 600 mls of ether is added, dropwise, to a slurry of 76.5 grams of magnesium (3.15 moles) in 600 mls of ether over a period of one hour at reflux under nitrogen. The resulting mixture is heated at reflux for 30 minutes and then cooled to 0° C. 1200 Grams of 20% (wt/wt) sulfuric acid is slowly added with external cooling over a 30-minute period. After the addition is complete, two clear layers appear. A distillation head is placed on the flask and ether is distilled from the reaction mixture at atmospheric pressure to a pot temperature of 90° C. 300 Mls of isopropyl alcohol is added to the reaction mixture. Sulfuric acid (100 grams) is added slowly and the resulting solution is heated to reflux for 8 hours. At the end of this period, the reaction mass is cooled. 500 Ml of water and 200 ml of toluene is added thereto with stirring. The phases are allowed to separate and the aqueous phase is discarded. The organic phase is washed twice with $H_2O$, with sufficient sodium carbonate added to the second wash to adjust to pH to 7–8. Distillation of the organic layer affords 286 grams of product (b.p. 90° C. at 4 mm).

The NMR and IR spectra show fraction 11 of the distillation.

Figure 4:
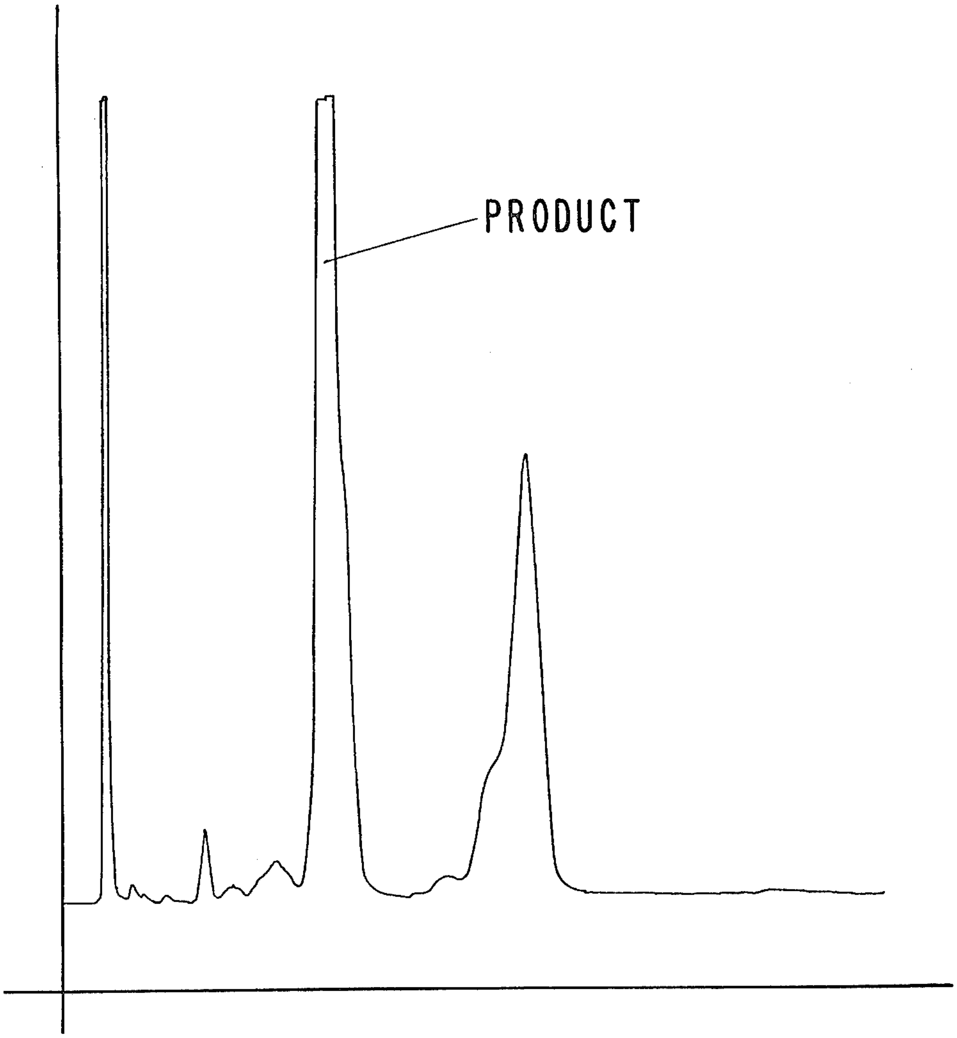
FIG. 4 is the GLC profile for the compound produced according to Example II, 3(2'-propenyl)-1,5-dimethyl-2-oxabicyclo[2.2.2]octane.
Figure 5:
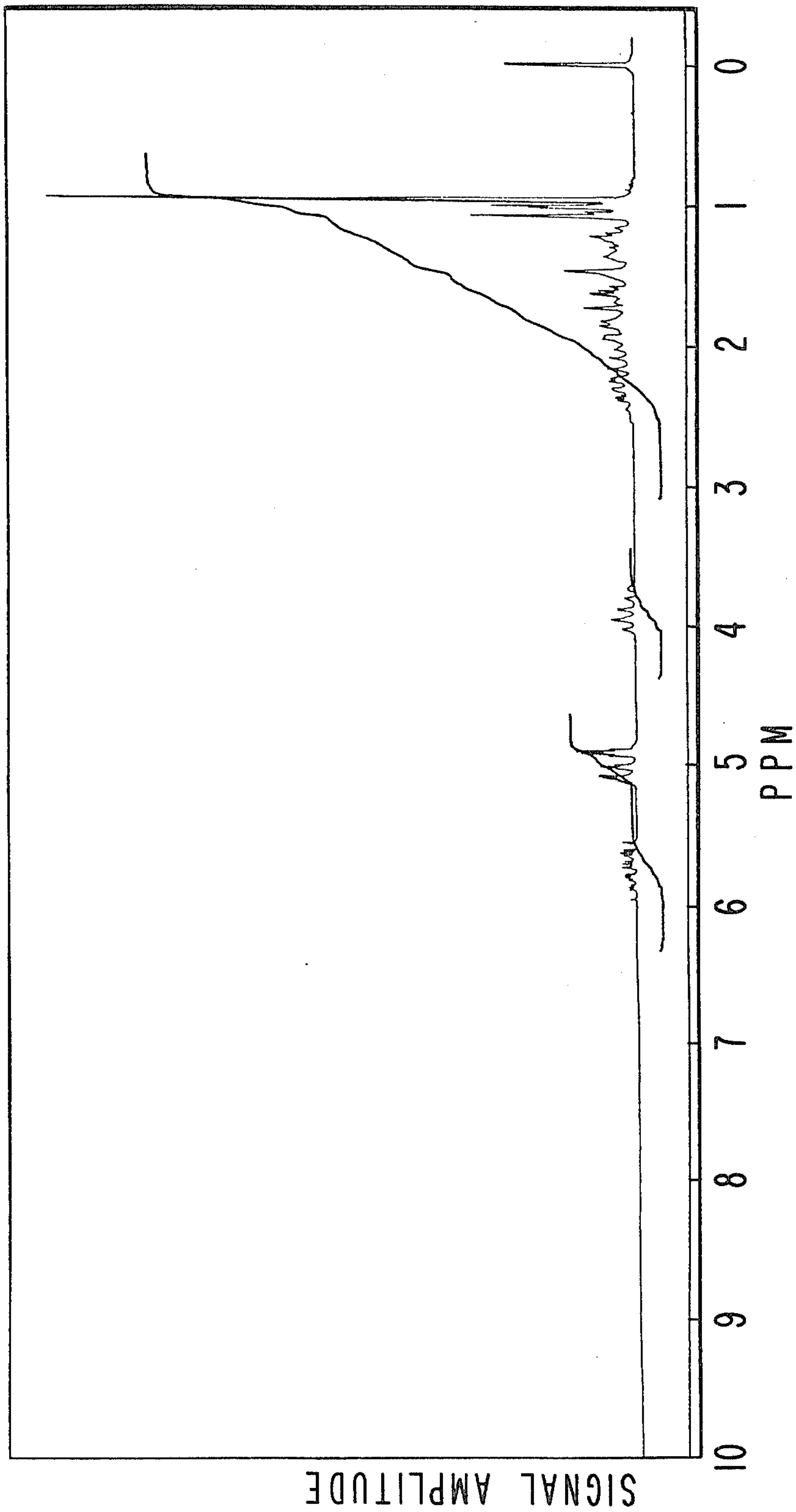
FIG. 5 is the NMR spectrum for the compound produced according to Example II.
Figure 6:
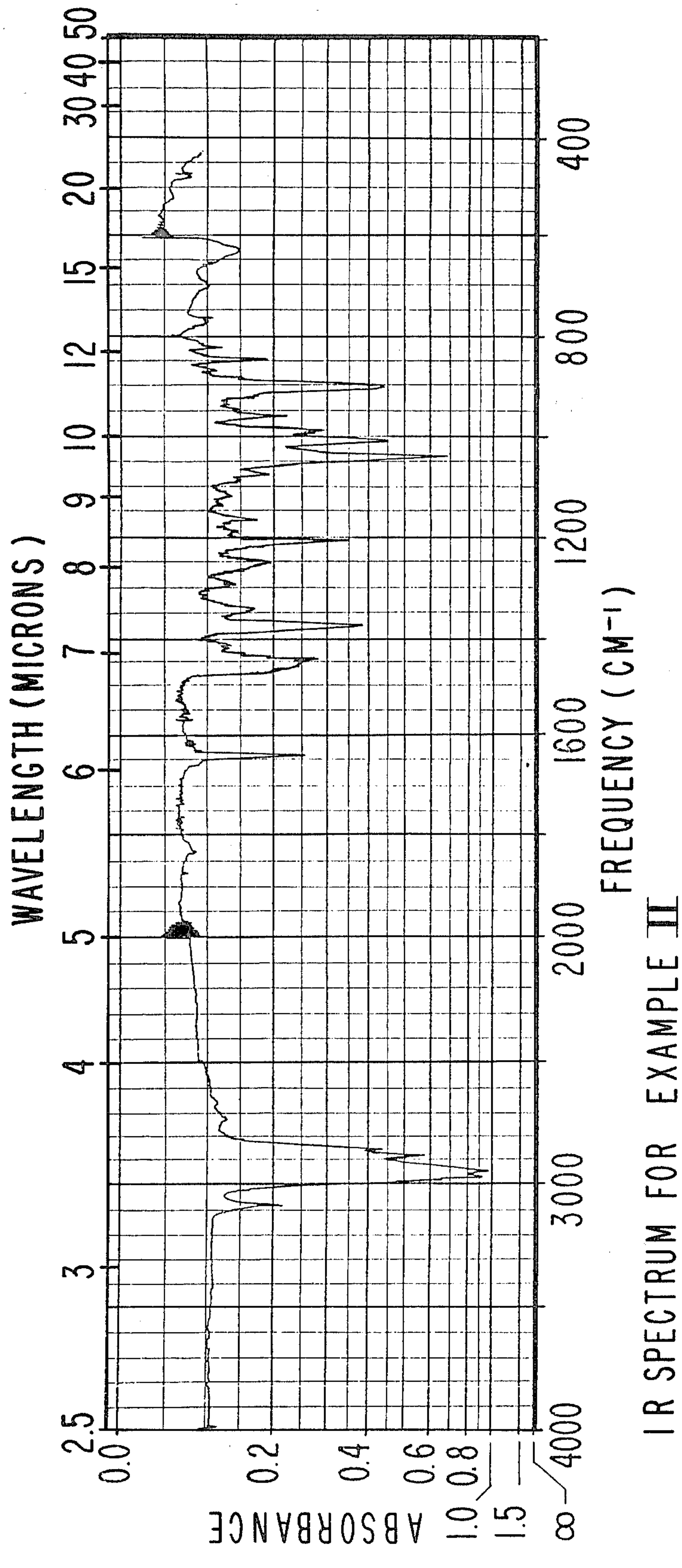
FIG. 6 is the infrared spectrum for the compound produced according to Example II.

FIG. 4 is the GLC profile for the reaction product (Conditions: 180° isothermal; Se-30 column). The NMR spectrum for the resulting reaction product is set forth in FIG. 5. The infrared spectrum for the resulting reaction product is set forth in FIG. 6.

EXAMPLE III

PREPARATION OF 1-METHYL-3-n-PENTYL-b 2-OXABICYCLO[2.2.2]OCTANE

Reaction:

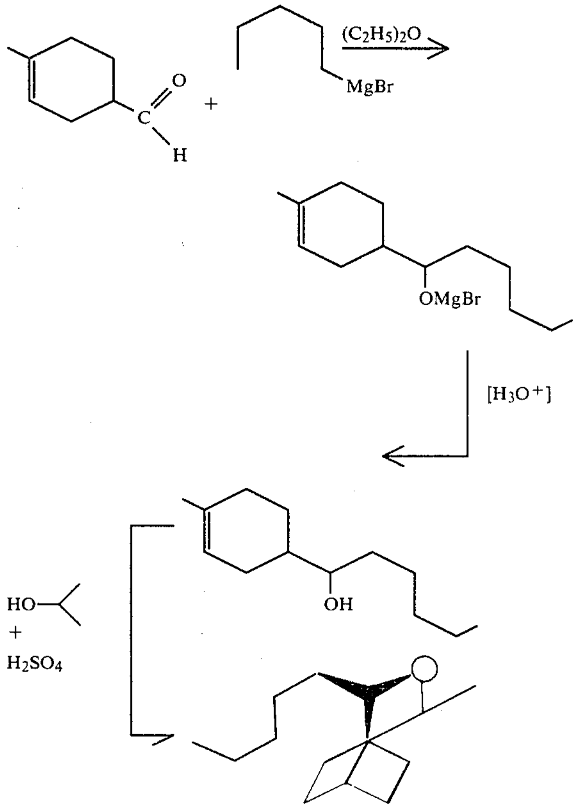

A solution of pentyl magnesium bromide in ether is prepared by dropwise adding a solution of b 525 grams (3.45 moles) of 1-bromopentane in 600 mls of dry ether to a stirred slurry of 76.5 grams of magnesium (3.15 moles) in 700 mls of dry ether under nitrogen at reflux. The resulting solution is stirred at reflux for 30 minutes. A solution of 378 grams of 1-methyl-3-cyclohexenyl carboxaldehyde (3 moles) in 200 mls of ether is then added to the reaction mixture over a period of one hour at reflux under nitrogen. The resulting slurry is heated at reflux for 30 minutes and then cooled to 0° C. 1400 Mls of 10% aqueous hydrochloric acid is slowly added with external cooling over a 30-minute period. After the addition is complete, two clear layers appear. A distillation head is placed on the flask and ether is distilled from the reaction mixture at atmospheric pressure to a pot temperature of 90° C. 200 Grams of isopropyl alchol is added to the reaction mixture. Sulfuric acid (200 grams) is added slowly and the resulting solution is heated to reflux for hours. At the end of this period, the reaction mass is coolled. 500 Ml of water and 200 ml of toluene is added thereto with stirring. The phases are allowed to separate and the aqueous phase is discarded. The organic phase is washed twice with $H_2O$, with sufficient sodium carbonate added to the second wash to adjust to pH to 7-8. Distillation of the organic layer affords 206 grams of product (b.p. 125° C., 4 mm).

The NMR and IR spectra shown fraction 17 of the distillation.

Figure 7:
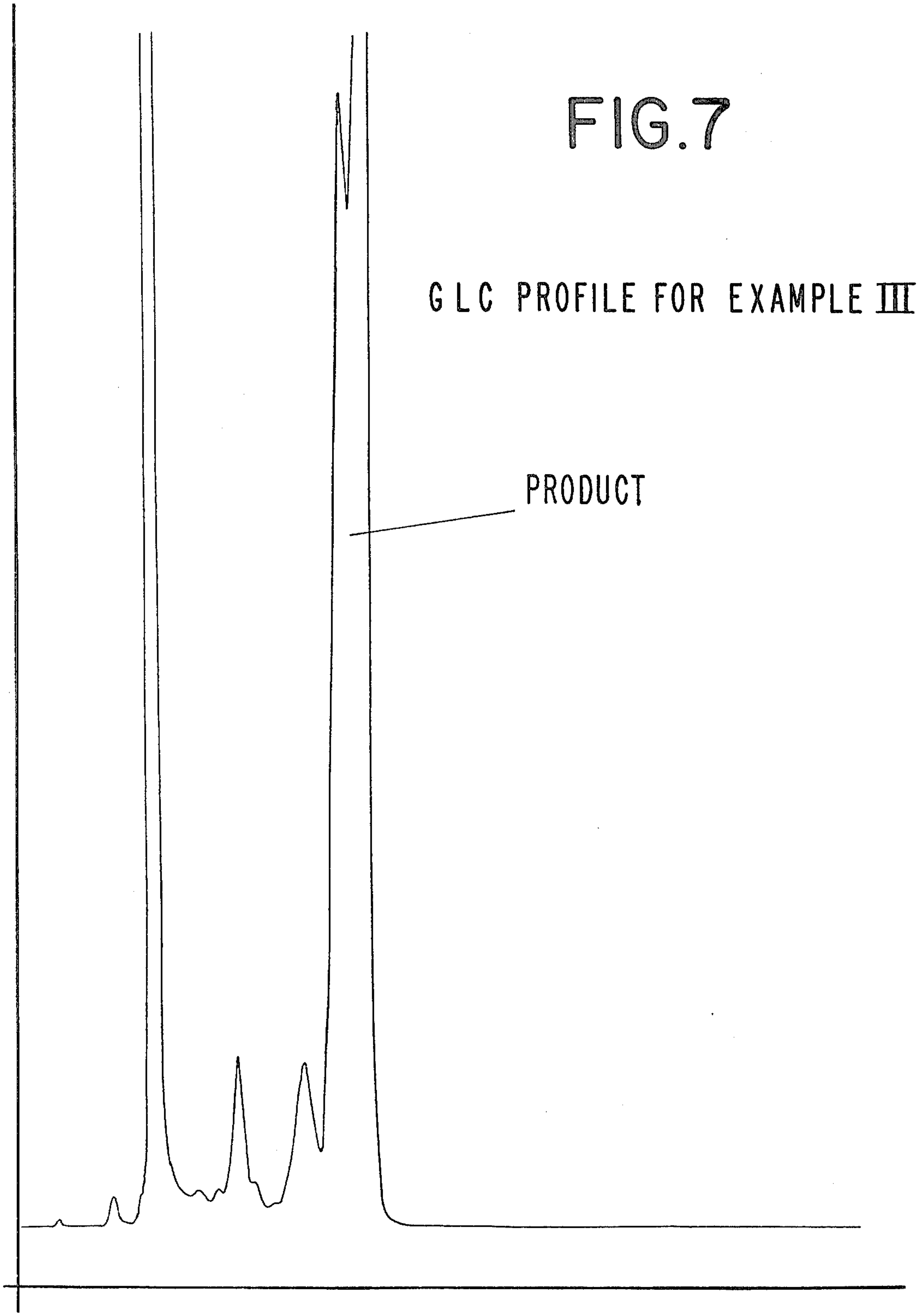
FIG. 7 is the GLC profile for the compound produced according to Example III, 3-n-pentyl-1-methyl-2-oxabicyclo [2.2.2]octane.
Figure 8:
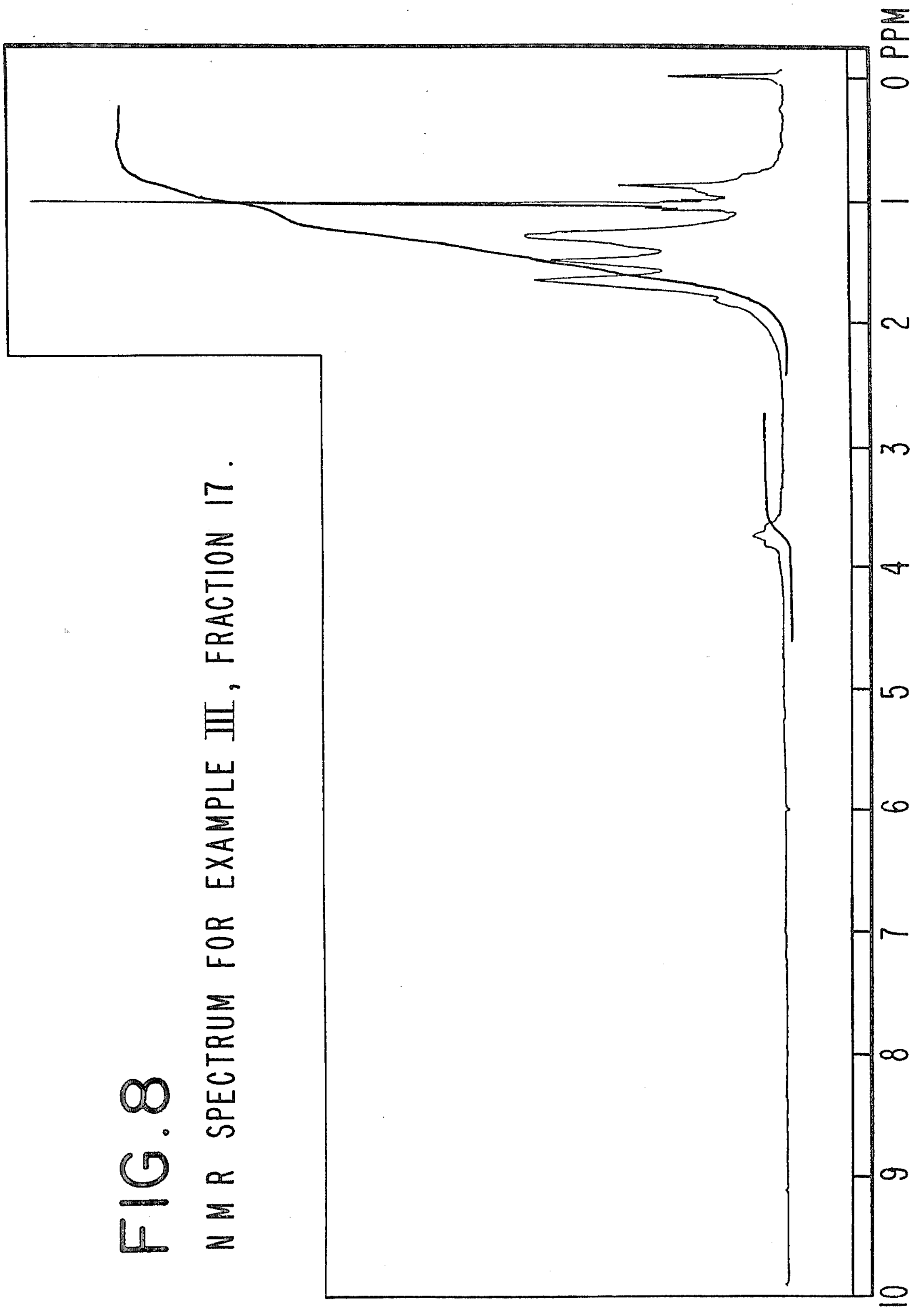
FIG. 8 is the NMR spectrum for fraction 17 of the distillate of the product produced according to Example III.
Figure 9:
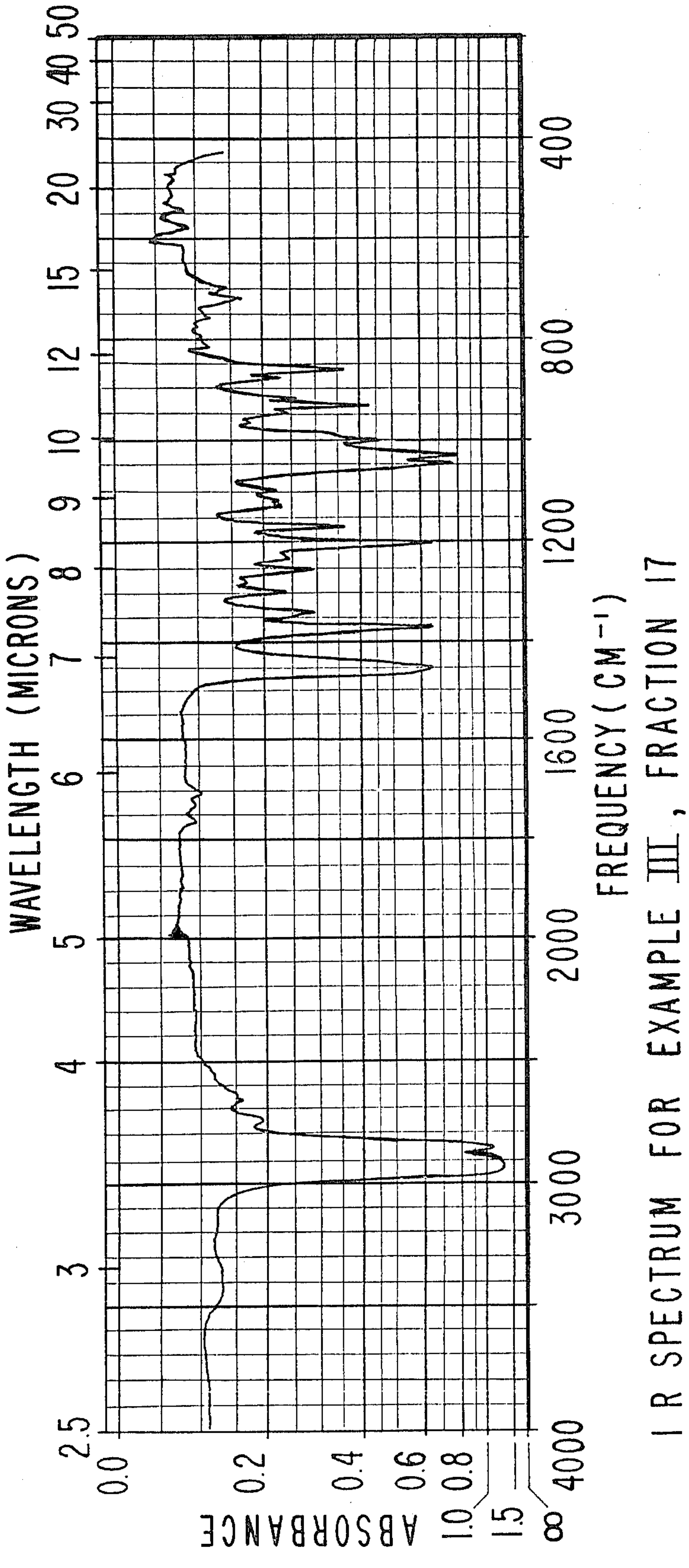
FIG. 9 is the infrared spectrum for fraction 17 of the distillate of the product produced according to Example III.

FIG. 7 is the GLC profile for the reaction product (conditions: 180° isothermal; SE-30 column). The NMR spectrum for the resulting reaction product is set forth in FIG. 8. The infrared spectrum for the resulting reaction product is set forth in FIG. 9.

EXAMPLE IV

CHOCOLATE FORMULATION

The following chocolate formulation is prepared:

| Ingredients | Parts by Weight |
|---|---|
| Dimethoxy Phenol (10% in food grade ethanol) | 0.5 |
| Amyl Acetate | 0.1 |
| Amyl Cinnamate | 0.1 |
| Gamma-Butyrolactone | 0.2 |
| Furfural | 0.05 |
| Benzaldehyde | 0.05 |
| Trimethyl pyrazine | 0.05 |
| Phenyl acetic acid | 0.35 |
| Isovaleraldehyde | 1.6 |
| Ethyl maltol | 12.0 |
| Ethyl vanillin | 20.0 |
| 1,2-Propylene glycol (USP) | 165.0 |
| Natural cocoa extract | 800.0 |

The basic chocolate flavor is divided into two parts. To a first part, 0.05% of 1-methyl-3-n-pentyl-2-oxabicyclo-[2.2.2]octane prepared according to Example III is added. To the second part, nothing is added. The two formulations are then evaluated by a bench panel of three experts. The chocolate flavor with the addition of the 1-methyl-3-n-pentyl-2-oxabicyclo[2.2.2]octane has a more cocoa powder aroma and taste with an additional touch of a "liver-like" fermented character found in high quality cocoa. These notes make the flavor more natural and more desirable. Therefore, the flavor formulation containing the 1-methyl-3-n-pentyl-2-oxabicyclo[2.2.2]octane is preferred unanimously by the members of the bench panel.

EXAMPLE V

RASPBERRY FLAVOR FORMULATION

The following basic raspberry formulation is produced:

| Ingredient | Parts by Weight |
|---|---|
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |

The above formulation is divided into two parts. To the first part is added at the rate of 1%, 3-allyl-1,5-dimethyl-2-oxabicyclo[2.2.2]octane prepared according to Example II. To the second part of this formulation nothing is added. Both formulations are compared in water at the rate of 100 ppm and evaluated by a bench panel of experts in the flavor field. All members of the bench panel state that the flavor containing the 3-allyl-1,5-dimethyl-2-oxabicyclo[2.2.2]octane has a more raspberry kernel note and a more raspberry juice character. In addition, the aroma of the formulation containing the 3-allyl-1,5-dimethyl-2-oxabicyclo[2.2.2]octane is substantially stronger than the flavor without the oxabicyclooctane derivative. Therefore, the flavor with the addition of the 3-allyl-1,5-dimethyl-2-oxabicyclo[2.2.2]oxtane is unanimously preferred by the bench panel.

EXAMPLE VI

TOMATO JUICE FORMULATION

The following tomato juice formulation is prepared by admixing the following ingredients:

| Ingredient | Parts by Weight |
|---|---|
| Maltol | 2 |
| Vanillin | 20 |
| Ethyl vanillin | 3 |
| Anisaldehyde (1% in propylene glycol) | 1 |
| Heliotropin (10% in propylene glycol) | 1 |
| Ethanol (95%) | 12 |
| Propylene glycol | 60 |
| TOTAL - | 100 |

To a canned tomato juice (manufactured by Campbell Soup Company of Camden, New Jersey; ingredients: pure tomato juice, slightly salted) at the rate of 2 ppm is added 1,5-dimethyl-3-(2'-butyl)-2-oxabicyclo[2.2.2]octane prepared according to Example I.

The fomulation with said 2-oxabicyclo[2.2.2]octane added is evaluated by a bench panel of three members. The panel concludes that the spicey notes are increased with more black pepper notes added both in aroma and taste, the aftertaste being fuller and pleasantly longer lasting.

EXAMPLE VII

A. POWDER FLAVOR FORMULATION

20 Grams of the flavor composition of Example V is emulsified in a solution containing 300 gm gum acacia and 700 gm water. The emulsion is spray-dried with a Bowen Lab Model Drier utilizing 260 c.f.m. of air with an inlet temperature of 500° F., an outlet temperature of 200° F. and a wheel speed of 50,000 rpm.

B. SUSTAINED RELEASE FLAVOR

The following mixture is prepared:

| Ingredients | Parts by Weight |
|---|---|
| Liquid raspberry flavor composition of Example V | 20 |
| Propylene glycol | 9 |
| Cab-O-Sil ® M-5 (Brand of silica produced by the Cabot Corporation of 125 High Street, Boston, Mass. 02110; Physical Properties: Surface Area: 200 $m^2$gm Nominal particle size: 0.012 microns Density: 2.3 lbs/cu.ft.) | 5.00 |

The Cab-O-Sil is dispersed in the liquid raspberry flavor compositions of Example V with vigorous stirring, thereby resulting in a viscous liquid. 71 Parts by weight of the powder flavor composition of Part A, supra, is then blended into the said viscous liquid, with stirring, at 25° C. for a period of 30 minutes resulting in a dry, free flowing sustained release flavor powder.

EXAMPLE VIII

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example V is added to the solution which is then homogenized to form an emulsion having particle size typically in the range of 2-5 microns. This material is kept at 120° F. under which conditions the gelatin will not jell.

Coacervation is induced by adding slowly and uniformly 40 parts by weight of a 20% aqueous solution of sodium sulphate. During coacervation the gelatin molecules are deposited uniformly about each oil droplet as a nucleus.

Gelatin is effected by pouring the heated coacervate mixture into 1,000 parts by weight of 5% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE IX

CHEWING GUM

100 Parts by weight of chicle are mixed with 4 parts by weight of the flavor prepared in accordance with Example VII. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting raspberry flavor.

EXAMPLE X

CHEWING GUM

100 Parts by weight of chicle are mixed with 18 parts by weight of the flavor prepared in accordance with Example VIII. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting raspberry flavor.

EXAMPLE XI

TOOTHPASTE FORMULATION

The following separate groups of ingredients are prepared:

| Parts by Weight | Ingredient |
|---|---|
| Group "A" | |

-continued

| Parts by Weight | Ingredient |
|---|---|
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalsium Phosphate (Dihydrate) |
| Group "C" | |
| 2.000 | Sodium N-Lauroyl Sarcosinate (foaming agent) |
| Group "D" | |
| 1.200 | Flavor Material of Example VII |
| 100.00 - TOTAL | |

PROCEDURE:

1. The ingredients in Group "A" are stirred and heated in a steam jacketed kettle to 160° F.
2. Stirring is continued for an additional three to five minutes to form a homogeneous gel
3. The powders of Group "B" are added to the gel, while mixing, until a homogeneous paste is formed
4. With stirring, the flavor of "D" is added and lastly the sodium-n-lauroyl sarcosinate
5. The resultant slurry is then blended for one hour. The completed paste is then transferred to a three roller mill and then homogenized and finally tubed.

The resulting toothpaste when used in a normal tooth-brushing procedure yields a pleasant raspberry flavor, of constant strong intensity throughout said procedure (1-1.5 minutes).

EXAMPLE XII

CHEWABLE VITAMIN TABLETS

The flavor material produced according to the process of Example VII is added to a Chewable Vitamin Tablet. Formulation at a rate of 10 gm/Kg which Chewable Vitamin Tablet formulation is prepared as follows:

In a Hobart Mixer, the following materials are blended to homogeneity:

| | Gms/1000 Tablets |
|---|---|
| Vitamin C (ascorbic acid) as ascorbic acid-sodium ascorbate mixture 1:1 | 70.11 |
| Vitamin $B_1$ (thiamine mononitrate) as Rocoat ® thiamine mononitrate 33⅓% (Hoffman La Roche) | 4.0 |
| Vitamin $B_2$ (riboflavin) as Rocoat ® riboflavin 33⅓% | 5.0 |
| Vitamin $B_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% | 6.6 |
| d-Biotin | 0.044 |
| Flavor of Example VII | (as indicated above) |
| Certified lake color | 5.0 |
| Sweetener-sodium saccharin | 1.0 |

-continued

| | Gms/1000 Tablets |
|---|---|
| Magnesium stearate lubricant | 10.0 |
| Mannitol q.s. to make | 500.0 |

Premliminary tablets are prepared by slugging with flatfaced punches and grinding the slugs to 14 mesh. 13.5 Gm dry Vitamin A Acetate and 0.6 gm Vitamin D are then added as beadlets. The entire blend is then compressed using concave punches at 0.5 gm each.

Chewing of the resultant tablets yields a pleasant, long-lasting, consistently strong raspberry flavor with lime nuances for a period of 12 minutes.

EXAMPLE XIII

The following mixture is prepared:

| Ingredients | Parts by Weight |
|---|---|
| Phenylacetic acid | 70.0 |
| Coumarin | 20.0 |
| Phenylethylphenyl acetate | 100.0 |
| Phenyl ethyl alcohol | 5.0 |
| Benzyl benzoate | 100.0 |
| Dimethylphenylethyl carbinol | 10.0 |
| Methyl anthranilate | 5.0 |
| Beta ionone | 10.0 |
| 3-Allyl-1,5-dimethyl-2-oxabicyclo [2.2.2]octane prepared according to Example II | 30.0 |

The 3-allyl-1,5-dimethyl-2-oxabicyclo[2.2.2]octane prepared according to Example II imparts the green, minty, caraway-like, tagette nuances to this honey fragrance while also getting it a basil topnote.

EXAMPLE XIV

PREPARATION OF A COSMETIC POWDER COMPOSITION

A cosmetic powder is prepared by mixing in a ball mill, 100 g of talcum powder with 0.25 g of the perfume composition prepared according to Example XIII. It has an excellent, minty, green, herbaceous, caraway, basil aroma.

EXAMPLE XV

PERFUMED LIQUID DETERGENT

Conentrated liquid detergents (Lysine salt of n-dodecylbenzene sulfonic acis as more specifically described in U.S. Pat. No. 3,948,818 issued on April 6, 1976) with green, minty, herbaceous, caraway, basil aroma nuances are prepared containing 0.10%, 0.15% and 0.20% of the fragrance prepared according to Example XIII. They are prepared by adding and homogeneously mixing the appropriate quantity of fragrance formulation prepared according to Example XIII in the liquid detergent. The detergents all possess excellent green, minty, herbaceous, caraway, basil aromas, the intensity increasing with greater concentrations of perfume composition of Example XIII.

EXAMPLE XVI

PREPARATION OF A COLOGNE AND HANDKERCHIEF PERFUME

The composition prepared according to Example XIII is incorporated into a cologne at concentration of 2.0%, 2.5%, 3.0%, 4.0%, 4.5% and 5.0% in 85% aqueous food grade ethanol; and into a handkerchief perfume at concentration of 15%, 20%, 25% and 30% (in 95% aqueous food grade ethanol). A distinctive and definite green, herbaceous, minty, caraway, basil aroma is imparted to the cologne and to the handkerchief perfume at all levels indicated above.

EXAMPLE XVII

PREPARATION OF SOAP COMPOSITION

One hundred grams of soap chips are mixed with one gram of the formulation of Example XIII until homogeneous compositions are obtained. In each of the cases, the homogeneous compositions are heated under three atmospheres pressure at 180° C. for a period of three hours and the resulting liquids are placed into soap molds. The resulting soap cakes, on cooling, manifest green, minty, herbaceous, caraway, basil aromas.

EXAMPLE XVIII

PREPARATION OF A SOLID DETERGENT COMPOSITION

A detergent is prepared from the following ingredients according to Example I of Canadian Pat. No. 1,007,943:

| | Percent by Weight |
|---|---|
| "Neodol 45-11-38 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free"detergent. A total of 100 grams of this detergent is admixed with 0.15 grams of the honey base perfume of Example XIII. The detergent sample has an excellent green, minty, herbaceous, caraway, basil aroma.

EXAMPLE XIX

PREPARATION OF A COSMETIC POWDER COMPOSITION

A cosmetic powder is prepared by admixing in a ball mill, 100 g of talcum powder with 0.25 g of 3-allyl-1,5-dimethyl-2-oxabicyclo[2.2.2]octane prepared according to Example II and 0.25 g of 1,5-dimethyl-3-(2'-butyl)-2-oxabicyclo[2.2.2]octane prepared according to Example I. The resulting cosmetic powder has an excellent green, minty, herbaceous, caraway-like aroma with basil nuances.

EXAMPLE XX

PERFUMED LIQUID DETERGENT

Concentrated liquid detergents (Lysine salt of n-dodecylbenzene sulfonic acid as more specifically described in U.S. Pat. No. 3,948,818 issued on April 6, 1976) with green, minty, herbaceous and caraway aroma notes and basil topnotes are prepared containing 0.10%, 0.15%, 0.20% and 0.25% of a 50-50 mixture of 1,5-dimethyl-3-(2'-butyl)-2-oxabicyclo[2.2.2]octane prepared according to Example I and 3-allyl-1,5-dimethyl-2-oxabicyclo[2.2.2]octane prepared according to Example II. They are prepared by adding and homogeneously mixing the appropriate quantity of the mixture of 1,5-dimethyl-3-(2'-butyl)-2-oxabicyclo[2.2.2]octane and 3-allyl-1,5-dimethyl-2-oxabicyclo[2.2.2]octane in the liquid detergent. The detergents all possess green, minty, herbaceous and caraway-like aroma nuances with basil topnotes, the intensity of each of the foregoing characteristics increasing with greater concentrations of 50-50 mixture of 1,5-diemthyl-3-(2'-butyl)-2-oxabicyclo[2.2.2]octane and 3-allyl-1,5-dimethyl-2-oxabicyclo[2.2.2]octane.

EXAMPLE XXI

PREPARATION OF COLOGNES AND HANDKERCHIEF PERFUMES

3-Allyl-1,5-dimethyl-2-oxabicyclo[2.2.2]octane prepared according to Example II is incorporated into colognes at concentrations of 2.0%. 2.5%, 3.0%, 3.5%, 4.0% and 4.5% in 85% aqueous food grade ethanol; and into handkerchief perfumes at concentrations of 15%, 20%, 25% and 30% (in 95% aqueous ethanol). Distinctive minty, herbaceous and caraway aroma nuances with basil topnotes are imparted to the colognes and to the handkerchief perfumes at various above levels indicated.

EXAMPLE XXII

PREPARATION OF COLOGNES AND HANDKERCHIEF PERFUMES 1,5-Dimethyl-3-(2'-butyl)-2-oxabicyclo[2.2.2]octane prepared according to Example I is incorporated into colognes at concentrations of 2.0%, 2.5%, 3.0%, 3.5%, 4.0% and 4.5% in 90% aqueous food grade ethanol; and into handkerchief perfumes at concentrations of 15%, 20%, 25% (in 95% aqueous food grade ethanol). Distinctive and definitive warm herbaceous aroma nuances with a black pepper type undertone are imparted to the colognes and to the handkerchief perfumes at the above-indicated levels.

EXAMPLE XXIII

Utilizing the procedure of Example I of column 15 of U.S. Pat. No. 3,623,396, a nonwoven cloth substrate useful as a dryer-added fabric-softening article of manufacture is prepared wherein the substrate, the substrate coating and the outer coating and the perfuming material are as follows:

1. a water "dissolvable"paper ("Dissolvo Paper").
2. Adogen 448 (m.p. about 140° F.) as the substrate coating; and
3. An outer coating having the following formulation (m.p. about 150° F.):
   57 percent $C_{20-22}$ HAPS
   22 percent isopropyl alcohol
   20 percent antistatic agent
   1 percent of the oxabicyclooctane derivative of our invention as set forth in the Table I below and giving rise to the aroma nuances as set forth in said Table I below:

TABLE I

| NAME OF COMPOUND | FRAGRANCE CHARACTERISTICS |
|---|---|
| 1,5-Dimethyl-3-(2'-butyl)-2-oxabicyclo[2.2.2]octane | A warm herbaceous aroma with a black pepper undertone. |
| 3-Allyl-1,5-dimethyl-2-oxabicyclo[2.2.2]octane | A minty, herbaceous, caraway aroma with basil nuances. |
| 3-n-pentyl-1-methyl-2-oxabicyclo[2.2.2]octane | A sweet, green, anisic-like aroma. |

Fabric-softening compositions prepared as set forth above having the above aroma characteristics essentially consist of a substrate having a weight of about 3 grams per 100 squre inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aromas as set forth in Table I above are imparted in a pleasant manner to the head space in the dryer on operation thereof using the said dryer added fabric softening nonwoven fabric.

What is claimed is:

1. A process for augmenting or enhancing the aroma of a perfumed article selected from the group consisting of fabric softener compositions, and fabric softener articles comprising the step of intimately admixing with a fabric softener article coating, or a fabric softener composition, an aroma augmenting or enhancing quantity of at least one cyclic chemical compound having a structure selected from the group consisting of:

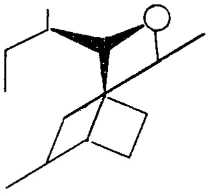
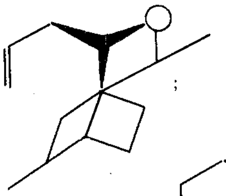
;
; and
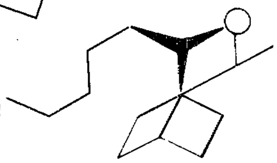

2. The process of claim 1 wherein the cyclic chemical compound has the structure:

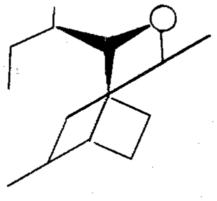

3. The process of claim 1 wherein the cyclic chemical compound has the structure:

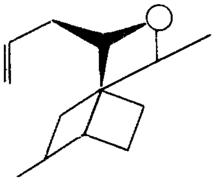

4. The process of claim 1 wherein the cyclic chemical compound has the structure:

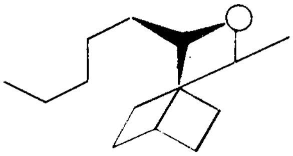

5. A fabric softener article comprising a non-woven cloth substrate and a coating for said substrate and intimately admixed with said coating for said substrate an aroma augmenting of enhancing quantity of at least one compound having a structure selected from the group consisting of:

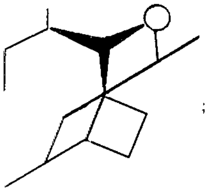
; and
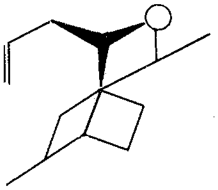

* * * * *